United States Patent
Harte

(10) Patent No.: US 11,783,936 B2
(45) Date of Patent: Oct. 10, 2023

(54) COMPUTER-AIDED DIAGNOSTICS USING DEEP NEURAL NETWORKS

(71) Applicant: Aidence B.V., Amsterdam (NL)

(72) Inventor: Mark-Jan Harte, Amsterdam (NL)

(73) Assignee: AIDENCE B.V., Amsterdam (NL)

( * ) Notice: Subject to any disclaimer, the term of this patent is extended or adjusted under 35 U.S.C. 154(b) by 352 days.

(21) Appl. No.: 16/637,525

(22) PCT Filed: Aug. 10, 2018

(86) PCT No.: PCT/EP2018/071830
§ 371 (c)(1),
(2) Date: Feb. 7, 2020

(87) PCT Pub. No.: WO2019/030410
PCT Pub. Date: Feb. 14, 2019

(65) Prior Publication Data
US 2020/0219609 A1 Jul. 9, 2020

(30) Foreign Application Priority Data
Aug. 10, 2017 (NL) ........................ 2019410

(51) Int. Cl.
*G16H 30/40* (2018.01)
*G16H 15/00* (2018.01)
(Continued)

(52) U.S. Cl.
CPC ............... *G16H 30/40* (2018.01); *G06N 3/04* (2013.01); *G16H 15/00* (2018.01); *G16H 50/20* (2018.01)

(58) Field of Classification Search
CPC ........ G16H 30/40; G16H 15/00; G16H 50/20; G06N 3/04
See application file for complete search history.

(56) References Cited

U.S. PATENT DOCUMENTS 8,908,948 B2 * 12/2014 Fan ................ G06T 7/143
 382/128
98,589,374  3/2017 Gao et al.
(Continued)

FOREIGN PATENT DOCUMENTS

CN  106897573 A  6/2016
CN  106909778 A  6/2017
WO  2016007518 A1  1/2016

OTHER PUBLICATIONS

International Search Report and Written Opinion for corresponding International application No. PCT/EP2018/071830; dated Oct. 11, 2018 (12 pages).
(Continued)

*Primary Examiner* — Robert A Sorey
*Assistant Examiner* — Kimberly A. Sass
(74) *Attorney, Agent, or Firm* — Mendelsohn Dunleavy, P.C.

(57) ABSTRACT

A computer-implemented method for determining a pathology in 3D image data is describe wherein the method may comprise: receiving at least a first 3D image of a body part, the 3D image comprising voxels associated with a predetermined image volume; a first 3D convolutional neural network determining a position of a volume of interest (VOI) in the image volume of the first 3D image, the VOI being associated with a pathology of the body part, the VOI defining a sub-volume of the image volume; determining first VOI voxels by selecting voxels of the first 3D image that have a position within the VOI as determined by the first 3D convolution neural network and providing the first VOI voxels to the input of a second 3D convolutional neural network; the second 3D convolutional neural network, determining a target label value on the basis of at least the first VOI voxels, the target label value being indicative of the presence or absence of a pathology in the VOI; and, gener-
(Continued)

202 3D localizer training module ating a medical report by associating the target label value determined by the second 3D convolutional neural network with text and/or sentences representing a description of the pathology.

19 Claims, 12 Drawing Sheets

(51) Int. Cl.
    *G16H 50/20*     (2018.01)
    *G06N 3/04*     (2023.01)

(56) References Cited

U.S. PATENT DOCUMENTS

| | | | | |
|---|---|---|---|---|
| 9,916,538 | B2* | 3/2018 | Zadeh | A61B 5/7221 |
| 10,074,038 | B2* | 9/2018 | Hsieh | G06N 3/084 |
| 10,169,685 | B2* | 1/2019 | Chen | G06K 9/6254 |
| 10,542,249 | B2* | 1/2020 | Wang | G06N 3/043 |
| 2013/0083023 | A1* | 4/2013 | Fram | G06T 19/00 345/424 |
| 2016/0174902 | A1 | 6/2016 | Georgescu et al. | |
| 2017/0124415 | A1 | 5/2017 | Choi et al. | |

OTHER PUBLICATIONS

Cheng, Jie-Zhi, et al. "Computer-Aided Diagnosis with Deep Learning Architecture: Applications to Breast Lesions in US Images and Pulmonary Nodules in CT Scans." Scientific Reports 6.1 (2016): 24454 (13 pages).

Springenberg, Jost et al., "Striving for Simplicity: The All Convolutional Net", 3rd International Conference on Learning Representations, ICLR, 2015.

Notice of Reasons for Rejection for corresponding Japanese application No. 2020-529823; dated Oct. 3, 2022 (9 pages).

Notice of Reasons for Rejection for corresponding Japanese application No. 2020-529823; dated Jul. 3, 2023 (6 pages).

First Office Action for corresponding Chinese application No. 201880051722.6; dated Mar. 30, 2023 (35 pages) Machine Translation.

* cited by examiner

Final Report MR Knee L.

Physician: Radiologist X
Date of review: 01-09-2016

Patient: John Doe
Date of birth: YYYY-MM-DD
Number: 1234567890

Indication: Pain in the left knee

*Translation from Aidence CAD platform* ... ithout contrast

Findings

Menisci:
Large longitudinal meniscal tear of the posterior horn of the medial meniscus, reaching the tibial surface.

Cruciate Ligaments:
Intact

Collateral Ligaments:
Intact

Cartilage Damage
Normal aspect of cartilage

Other findings
Patellofemoral compartment intact

Conclusion: Longitudinal meniscal tear of the medial meniscus Ligaments and cartilage are intact.

Signing date: 01-09-2016

FIG. 10

COMPUTER-AIDED DIAGNOSTICS USING DEEP NEURAL NETWORKS

FIELD OF THE INVENTION

The invention relates to computer-aided diagnostics using deep neural networks, and, in particular, though not exclusively, to methods and systems for computer-aided diagnostics using deep neural networks and a computer program product for using such method.

BACKGROUND OF THE INVENTION

Computer-aided diagnosis (CAD) is a computerized procedure to provide an objective opinion for assisting in medical image interpretation and diagnosis. In such procedure medical images, e.g. MRI images, of a patient are offered to the input of a program that is configured to detect (i.e. localize) certain conspicuous structures and sections in the images and subsequently evaluate the detected structures and sections according to a pathology classification. Typically, conventional image processing techniques such as feature analysis and object tracking are used to examine the images and extract useful information out of them. The feature analysis however depends very much on the type of problem and the type of image data that need to be processed. In order to tackle these problems recently deep neural networks have been used for image analysis allowing direct detection and recognition of features in 2D images.

For example, Cheng et al, in "*Computer-Aided Diagnosis with Deep Learning Architecture: Applications to Breast Lesions in US Images and Pulmonary Nodules in CT Scans*", Nature Scientific Reports, 15 Apr. 2016, describe a study of computer-aided diagnosis for differential diagnosis of benign and malignant nodules/lesions using a specific deep neural network architecture called a 'Stacked Denoising Auto-Encoder' (SDAE). The deep neural network was trained using pre-selected regions in images (regions of interest or ROI) that include a labelled nodule or lesion. The study shows that the performance of the CAD system based on a deep neural network performed better than or at least matches some of the conventional texture-based CAD systems.

Hence, 2D medical images, e.g. DICOM 'slices', may be input to a trained deep neural network in order to diagnose pathologies. Anatomical structures however are not constrained to a 2D plane but have a 3D structure and it is advantageous for a doctor to receive information about a diagnosis in three dimensions. To learn these 3D structures, a 3D model is required. It would be beneficial to directly supply 3D image data instead of 2D image data to the input of a trained neural network.

However, extending deep neural network techniques from the 2D (pixel) space to the 3D (voxel) space and efficiently generating a trained deep network that can handle 3D image data with sufficient accuracy so that it can be used as a reliable diagnosis tool is not obvious and provides serious challenges due to the very large computational demands required by 3D modelling. For example, a typical MRI 2D 'slice' comprises 512*512=262K pixels, whereas the full 3D series (containing 200 'slices') includes 200*512*512=5.2 M voxels. Hence, for large 3D data sets, the amount of processing becomes heavy and often an unsurmountable burden which seriously inhibits practical applications on 3D image data sets.

US2016174902A1 describes an example of a computer-aided detection system for the detection of anatomical objects using so-called marginal space deep neural networks. The described system includes a series of trained deep neural networks wherein each neural network is trained for a certain parameter space with increased dimensionality, e.g. position, position-orientation, position-orientation-scale, etc. The deep neural network architecture uses so-called 'stacked denoising autoencoders' (SDAE) and a 'sparse adaptive deep neural network' (SADNN) in order to deal with the problem of handling large 3D volumes. Effectively, SADNN is a technique for simplifying the deep neural network so that the process becomes less computationally intensive. Such approach however may affect the accuracy of the system. Further, the system is configured for detecting anatomical objects. It is not capable of providing an objective opinion for assisting in medical image interpretation and diagnosis.

Hence, from the above it follows there is a need in the art for improved deep neural network based systems that allow efficient and accurate computer-aided diagnostics on the basis of a volume of voxels. In particular, there is a need in the art for improved deep neural network based systems that allow efficient and accurate detection, localization, classification and reporting of pathologies on the basis of a volume of voxels of a sequence of medical images.

SUMMARY OF THE INVENTION

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Functions described in this disclosure may be implemented as an algorithm executed by a microprocessor of a computer. Furthermore, aspects of the present invention may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber, cable, RF, etc., or any suitable combination of the foregoing. Computer program code for carrying out operations for aspects of the present invention may be written in any combination of one or more programming languages, including an object oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to one or more processors, in particular a (graphical) microprocessor, a central processing unit (CPU) or a graphical processing unit (GPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

It is an objective of the invention to reduce or eliminate at least one of the drawbacks known in the prior art. In an aspect the invention may relate to a computer-implemented method for determining a pathology in 3D image data comprising: receiving at least a first 3D image of a body part, the 3D image comprising voxels associated with a predetermined image volume; a first 3D convolutional neural network determining a position of a volume of interest (VOI) in the image volume of the first 3D image, the VOI being associated with a pathology of the body part, the VOI defining a sub-volume of the image volume; determining first VOI voxels by selecting voxels of the first 3D image that have a position within the VOI as determined by the first 3D convolution neural network and providing the first VOI voxels to the input of a second 3D convolutional neural network; the second 3D convolutional neural network, determining a target label value on the basis of at least the first VOI voxels, the target label value being indicative of the presence or absence of a pathology in the VOI.

Hence, the invention uses a first deep neural network to pre-process 3D image data that are used as 3D training data for a second deep neural network. The first deep neural network provides a positions associated with a VOI that contains a volume of the 3D image that may contain a pathology. This way, only relevant voxels of a 3D image may be used as input to a further deep neural network that is configured to generate a target label which can be associated with a particular pathology. The invention includes the application of fully 3D deep neural networks in order to use the anatomical 3D structure for pathology classification and thereby obtaining a higher performance, while also applying performance optimization in the form of 3D localization using a deep learning network in order to reduce the volume required to perform the pathology classification.

The pre-processing substantially reducing the amount of 3D image data of the training set that is relevant for the training process, thereby substantially improving the training time of the 3D neural network. Moreover, by removing irrelevant data, the complexity of the computation can be reduced. The invention therefore allows for more training iterations in a given time period thus resulting in a trained deep learning network that is capable of generating an improved disorder model. Considering that training time can grow to a week or more, such localization provides a substantial benefit.

Preferably, the neural networks may be trained to determine a pathology in body parts such as joints, in particular knees.

In an embodiment, the method may further comprise generating a medical report by associating the target label value determined by the second 3D convolutional neural network with text and/or sentences representing a description of the pathology. Hence, the target label may be linked to text strings that can be used to construct a text for a computer-generated medical report where the text provides information about the presence of one or more pathologies.

In an embodiment, the generating of the medical report may include if the target label value is within a predetermined first range, determining a first text string describing that the pathology, e.g. a meniscus tear, has been determined and if a target label value is within a predetermined second range, determining a second text string describing that a certain pathology, e.g. a meniscus tear, has not been determined.

In a further embodiment, the generating of the medical report may include inserting the first or second text string into a text string representing a report template.

In an embodiment, the method may further comprise: retrieving a 3D probability map associated with the VOI voxels from a convolutional layer of the second convolutional neural network and using the 3D probability map as input to a backpropagation process for generating a 3D saliency map associated with the VOI voxels. In an embodiment, the method may further comprise: generating an annotated 3D image of the pathology in the VOI by using the 3D saliency map to identify voxels in the VOI that made a substantial contribution to the determination of the target label value by the second 3D convolutional neural network. In an embodiment, the method may comprise inserting the annotated 3D image or one or more 2D slices of the annotated 3D image in the report. Hence, the invention also allows 3D visualization of a pathology in a VOI. Such visualization provides valuable information for an medical expert in the evaluation of the 3D images and the diagnosis.

In an embodiment, the first 3D image may include a sequence of images of a first image plane, preferably a sagittal image plane. In an embodiment, the method may further comprise: receiving a second 3D image of the body part, the second 3D image including a sequence of images of a second image plane, preferably a coronal image plane; determining second VOI voxels by selecting voxels of the second 3D image that have a position within the VOI; the second 3D convolutional neural network, determining a target label value on the basis of the first and second VOI voxels.

In an embodiment, the second 3D convolutional neural network may include at least a first plurality of 3D convolutional neural network layers forming a first pathway through the neural network and a second plurality of 3D convolutional neural network layers forming a second pathway through the second neural network.

In an embodiment, the first plurality of 3D convolutional neural network layers may be configured to process the first VOI voxels and the second plurality of 3D convolutional neural network layers may be configured to process the second VOI voxels.

In an embodiment, the first and/or second 3D convolutional neural network may include one or more noise layers.

In a further aspect, the invention may relate to a computer-implemented method for training one or more 3D deep neural networks in a system that is configured to determine a pathology in 3D image data.

In an embodiment, the method may comprise: a computer receiving a 3D image data training set of a medical study, the 3D image data training set comprising 3D images, a 3D image comprising voxels associated with a predetermined image volume and being associated with a medical report comprising computer-readable text parts and/or sentences indicative of a pathology in the 3D image; for each 3D image of the 3D image training data, forming a 3D bounding box on the basis 2D regions of interest (ROIs) in slices of the 3D image, the 3D bounding box forming a sub-volume in the image volume of the 3D image, the sub-volume defining a volume of interest (VOI); for each 3D image of the 3D image training data, determining the position of the VOI in the image volume and determining voxels that are positioned in the VOI; and, training a first 3D convolutional neural network using the voxels of each VOI as input and the position of VOI as target.

In an embodiment, the method may further comprise: for each 3D image of the 3D image training data, processing computer-readable text and/or phrases of the medical report associated with the VOI for producing a target label value, the target label value being indicative of the presence of absence of a pathology in the VOI; training a second 3D convolutional neural network using the voxels of the VOIs as input and the target label values associated with the VOIs as a target.

In an embodiment, processing computer-readable text and/or phrases may include: using a decision tree for describing how the presence or absence of one or more phrases and/or words determines the target label value.

In yet a further aspect, the invention may relate to a computer system adapted to determine a pathology in 3D image data. In an embodiment, the computer may comprise: a storage medium having computer readable program code stored therein, the code including a first and second 3D convolutional neural network, and one or more processors, preferably one or more microprocessors, coupled to the computer readable storage medium, wherein upon executing the computer readable program code, the system carrying out operations comprising: receiving at least a first 3D image of a body part, the 3D image comprising voxels associated with a predetermined image volume; the first 3D convolutional neural network determining a position of a volume of interest (VOI) in the image volume of the first 3D image, the VOI being associated with a pathology of the body part, the VOI defining a sub-volume of the image volume; determining first VOI voxels by selecting voxels of the first 3D image that have a position within the VOI as determined by the first 3D convolution neural network and providing the first VOI voxels to the input of the second 3D convolutional neural network; the second 3D convolutional neural network, determining a target label value on the basis of at least the first VOI voxels, the target label value being indicative of the presence or absence of a pathology in the VOI; and, generating a medical report by associating the target label value determined by the second 3D convolutional neural network with text and/or sentences representing a description of the pathology.

In an embodiment, the operations may further comprise: retrieving a 3D probability map associated with the VOI voxels from a convolutional layer of the second convolutional neural network and using the 3D probability map as input to a backpropagation process for generating a 3D saliency map associated with the VOI voxels; generating an annotated 3D image of the pathology in the VOI by using the 3D saliency map to identify voxels in the VOI that made a substantial contribution to the determination of the target label value by the second 3D convolutional neural network.

In an embodiment, the operations may further comprise: inserting the annotated 3D image or one or more 2D slices of the annotated 3D image in the report.

In an embodiment, the first 3D image may include a sequence of images of a first image plane, preferably a sagittal image plane. In an embodiment, the operations may further comprise: receiving a second 3D image of the body part, the second 3D image including a sequence of images of a second image plane, preferably a coronal image plane; determining second VOI voxels by selecting voxels of the second 3D image that have a position within the VOI; the second 3D convolutional neural network, determining a target label value on the basis of the first and second VOI voxels.

In an embodiment, the second 3D convolutional neural network may include at least a first plurality of 3D convolutional neural network layers forming a first pathway through the neural network and a second plurality of 3D convolutional neural network layers forming a second pathway through the second neural network.

In an embodiment, the first plurality of 3D convolutional neural network layers may be configured to process the first VOI voxels and the second plurality of 3D convolutional neural network layers may be configured to process the second VOI voxels.

The invention will be further illustrated with reference to the attached drawings, which schematically will show embodiments according to the invention. It will be understood that the invention is not in any way restricted to these specific embodiments.

BRIEF DESCRIPTION OF THE DRAWINGS

FIG. 10 depicts an example of a report that is generated using a system for computer-aided diagnostics according to an embodiment of the invention.

DETAILED DESCRIPTION

In this disclosure embodiments are described of computer systems and computer-implemented methods that use deep neural networks for detection, localisation, classification, reporting and visualisation of pathologies of an anatomical structure on the basis of 3D image data, e.g. 3D image data defined by one or more sequences of medical images such as MRI or CT images. These systems and methods are especially suitable for application in computer-aided detection and diagnostics.

A computer system according to the invention may comprise two modes, a training mode and an inference mode. When the system is in the training mode, a training process is executed wherein the system iteratively trains (optimizes) at least two deep neural networks on the basis of one or more training sets that includes 3D image data. A first trained deep neural networks, i.e. a database of a plurality (typical millions) of parameters describing the connections of the trained deep neural network, may represent a pathology model that is configured to generate a 3D computer-aided diagnosis and a second trained deep neural network that may represent a 3D localizer model that is configured to provide the location of 3D image data contained in a volume of interest (VOI) of the volume of the 3D image data (in short an image volume) of a training set. The use of these trained deep neural networks in computer-aided diagnostics and the training of these networks are described hereunder in more detail. When the system is in the inference mode, the computer system may execute a process wherein a new set of 3D image data of an anatomical structure (i.e. a data set other than the training set) may be offered to the input of the trained deep neural networks so that the deep neural networks can process the input data in order to accurately and efficiently detecting, localising and reporting a pathology in the new 3D image data.

Figure 1:
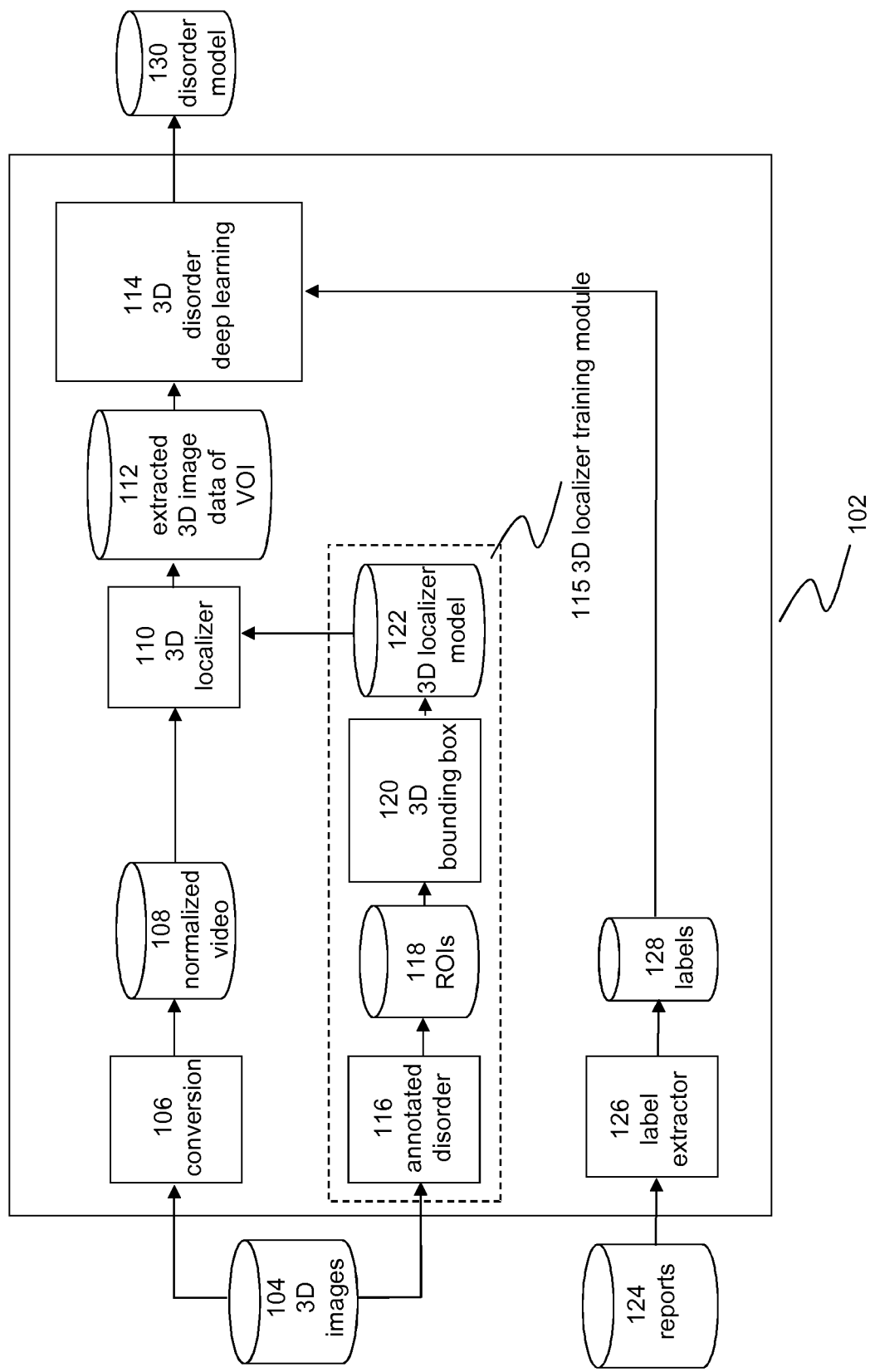
FIG. 1 schematically depicts a system for computer-aided diagnostics using deep neural networks according to an embodiment of the invention.

FIG. 1 schematically depicts a computer system for computer-aided diagnostics using deep neural networks according to an embodiment of the invention. In particular, FIG. 1 depicts a computer system for computer-aided diagnostics, wherein the system in a training mode. In this mode, a first 3D deep neural network 114 is trained on the basis of a training data set 104, i.e. a data set including 3D image data and, optionally, one or more other data types such as phrases and/or words 124 representing expert information on a pathology represented in the 3D image data of the training data set. The 3D image data may include voxels associated with a predetermined volume, which in short is referred to as an image volume. The training data set may include preselected 3D image data such as a sequence of MRI or CT images and relevant parts of radiological reports, e.g. in the form of computer-readable text files, associated with the preselected 3D image data.

During the training process, the training data set may be input to the first deep neural network in order to train the network iteratively. In an embodiment, the training data set may include one or more sequences of MRI images forming a 3D image data stack and representing the anatomy of part of a body (e.g. a knee) that has a predetermined pathology (e.g. a certain meniscal tear) and (relevant text parts of) one or more reports, e.g. radiological reports, associated with the training data, wherein the reports include information on a pathology that is diagnosed by an expert, e.g. a doctor or the like.

A known stochastic gradient descent optimization method may be used to learn the optimal values of the network parameters of the first deep neural network by minimizing a loss function which represents the deviation between the output of the deep neural network and a target label, e.g. a label identifying a pathology, representing the desired output for a predetermined input (i.e. the training set). When the minimization of the loss function converges to a certain value, the training process may be completed.

The first trained 3D neural network may represent a disorder model 130 that is capable of accurately classifying and reporting a pathology in 3D image data that is offered to the input of the trained network. Here, the classification may include generating a target label value, determining whether the target label value represents a positive result (e.g. meniscal tear detected) or negative result (no meniscal tear detected) and associating a computer-generated text and/or phrases representing a semantic representation of the positive or negative result. These text and/or phrases, at least a first text and/or phrases representing a semantic or textual representation, e.g. a first string of ascii codes, of the positive result and at least a second text and/or phrases representing a semantic or textual representation, e.g. a second string of ascii codes, of the negative result may be stored in a database of the system.

During the execution of the training process of the first 3D deep neural network, the computer system may pre-process the training data before feeding the data to the input of the first 3D deep neural network of the pathology model 114. The 3D image data of the training data set may include several sets of 3D image data associated with the same image volume, each set being generated using a different acquisition plane (e.g. sagittal or coronal acquisition plane) and pulse sequence (e.g. TE and TR times). In an embodiment, the data may include at least a first set of 3D image data generated based on a sagittal acquisition plane using repetition RE time and/or echo TE time and at least at least a second set of 3D image data generated based on a coronal acquisition plane using repetition RE time and/or echo TE time. Based on radiological expertise, one or more series may be selected as having the highest relevance for a pathology. These selected series may be used as a training data set. Typically, the images originate from different hospitals and thus may have different data formats, e.g. the DICOM format or the like. In that case, the image data first need to be converted to a standard format that is suitable for subsequent processing.

For example, in an embodiment, the MPEG-4 video format may be used for 3D image data storage and processing. Additionally, in an embodiment, a normalization process may be applied to the 3D image data, e.g. the image brightness may need to be normalized as this may be inconsistent across different series and/or studies. Known image data normalization processes may be used such as contrast-limited adaptive histogram equalisation. A conversion module 106 of the system may be adapted to execute the conversion and normalisation of the image data and store the normalized image data in a database 108.

A sequence of medical images may represent a 3D image of a particular scanned volume of a patient. In many cases however, it is not necessary for the computer system to train the first deep neural network on the basis of the entire 3D image data set, because there is no medical relevance to parts of it. For example, to diagnose a meniscal tear, it is not necessary to include 3D image data associated with the tibial and femoral bone. The amount of training time is linearly dependent on the number of voxels that determine the 3D image data volume. Thus, localizing the 2D area that contains the relevant information in each image of a series of images that form the 3D image data volume, may considerably reduce the size of the 3D training volume.

To that end, after converting the 3D image data of the training data set into a standardized and normalized data format, the computer system may feed the normalized 3D image data to the input of a 3D localizer 110 that comprises a second deep neural network that is trained to determine the position a so-called volume of interest (VOI) within the (normalized) image volume of the 3D image data, wherein the VOI defines a sub-volume in the image volume that contains the voxels of the anatomical structure that requires diagnosis. Hence, the 3D localizer 110 may comprise a second trained deep neural network representing a 3D localizer model for accurately determining the location of a VOI in the image volume that includes the anatomical structure for which a pathology needs to be diagnosed. In an embodiment, the VOI may be a 3D bounding box containing 3D image data (voxels). The 3D image data contained in the VOI are subsequently used as 3D image data for training the 3D deep neural network of the pathology model.

The 3D localizer thus pre-processes the 3D image data of the training set by substantially reducing the amount of 3D image data of the training set to 3D image data that are relevant for the training process. The 3D localizer thus substantially improves the training time of the 3D deep learning network 114. Moreover, by removing irrelevant data, the complexity of the computation can be reduced. The 3D localizer allows for more training iterations in a given time period thus resulting in a trained deep learning network that is capable of generating an improved disorder model. Considering that training time can grow to a week or more, such localization provides a substantial benefit.

As shown in FIG. 1, a 3D localizer training module 115 may be configured to separately train the deep neural network of the 3D localizer 110 on the basis of 3D localizer model 122 including positions of VOIs in the 3D image data of the training set. These VOIs may be derived from an annotated training data set 116 of 3D image data. ROIs 118 may be determined in slices of the annotated training set and a 3D bounding box may be determined using the ROIs, wherein the 3D bounding box 120 may represent a VOI, wherein each VOI may be associated with a position in the image volume. These positions may be represented in a suitable coordinate system for defining a 3D position x,y,z in the image volume. These positions may be used as target labels during training. The annotated data set may be selected from the training data set 104 that is used to train the 3D deep neural network of the pathology model.

In some embodiments (not shown), the training data may include at least a first set of 3D image data (a primary sequence of images associated with a first image plane in the image volume) and an associated second set of 3D image data (a secondary sequence of images associated with a second image plane in the image plane). 3D images such as 3D MRI or CT images of an anatomical object may be generated using different imaging planes, e.g. the coronal plane and the sagittal plane of an image volume. The combined use of 3D image data of different image planes enables accurate 3D image data reconstruction. In such case, the position of a voxel of 3D image data of the primary 3D image data set is linked to a position of a voxel of the secondary 3D image data set using a known coordinate mapping.

In an embodiment, the deep neural network of the 3D localizer may be trained to process one of the sequences of images, e.g. the primary 3D image data set. The target of the trained deep neural network of the 3D localizer, i.e. a first location of the first VOI in the volume of the primary 3D image data. Then, a coordinate mapping between the primary and secondary 3D image data may be used to determine a second location of a corresponding second VOI in the volume of the secondary 3D image data.

Figure 2:
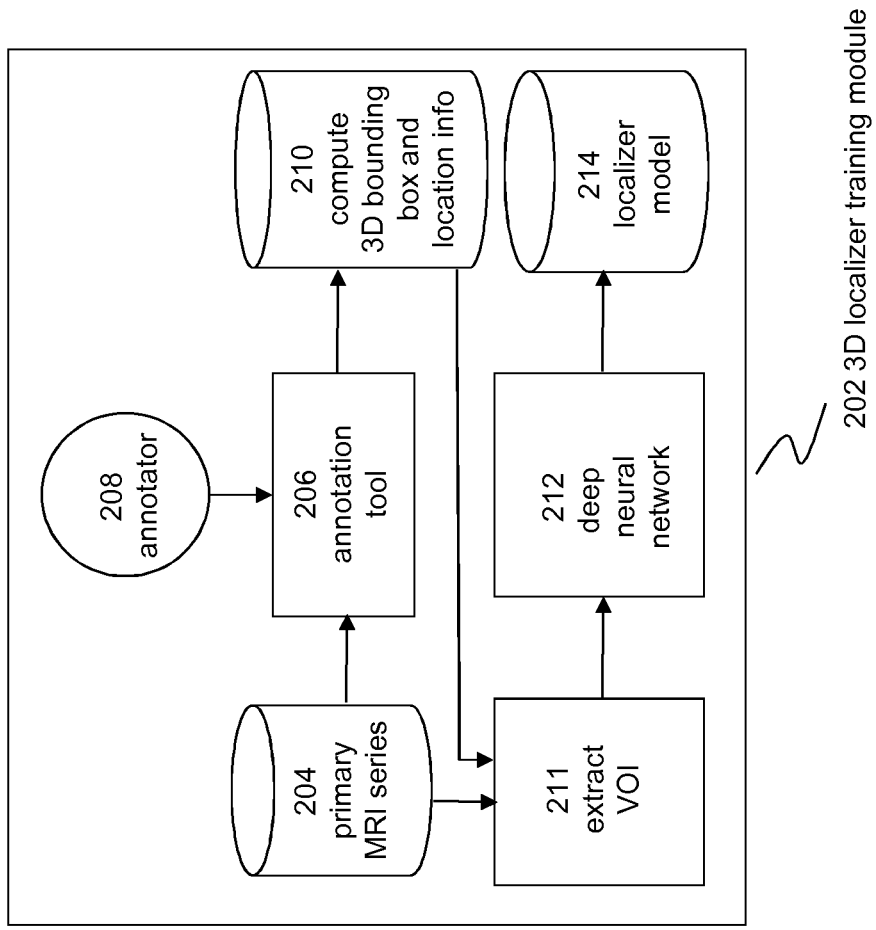
FIG. 2 schematically depicts a localizer module according to an embodiment of the invention.

FIG. 2 schematically depicts a 3D localizer training module according to an embodiment of the invention. In particular, FIG. 2 depicts an example of a 3D localizer training module that is configured to execute a training process for training a 3D deep neural network 212 so that is functions according to a desired localizer model 214 which generates a 3D position (e.g. in terms of coordinates x,y,z of a coordinate system associated with the 3D image volume) of a VOI containing the voxels of a particular pathology as its target.

The training process may include a step of selecting a training data set 204 of 3D image data, e.g. a sequence of medical images such as MRI images, for training the deep neural network of the 3D localizer. The selected training data set may be significantly smaller than the set required for training the 3D deep neural network of the pathology model.

The localizer training module 202 may comprise an annotation tool 206, e.g. a software application, that is configured to display sequences of images (slices) of the training data set and to annotate each slice by determining a 2D region of interest (ROI) in each slice, e.g. a planar closed polygon, that encompasses a predetermined anatomical structure that is the object of diagnosis. In an embodiment, the determination of the 2D ROIs may include an annotator 208 controlling a drawing tool that allows determining boundaries of an area, a ROI, in an image in which a predetermined anatomical structure is located.

Figure 3:
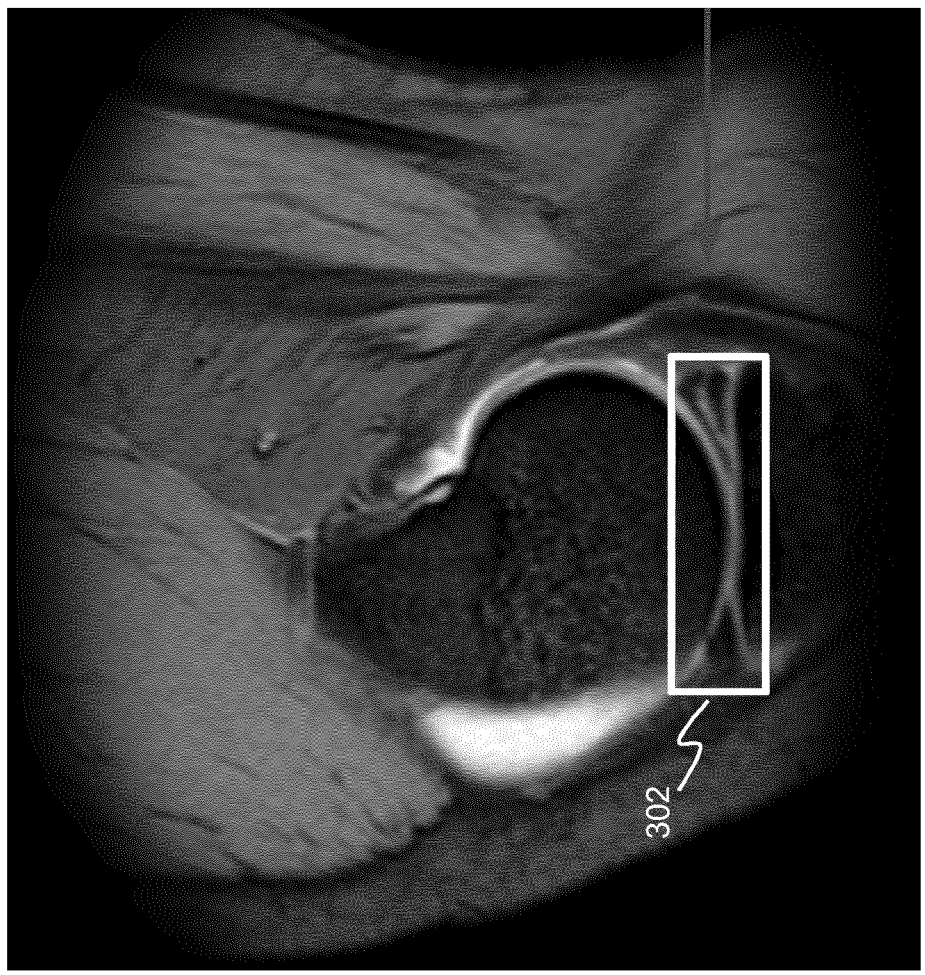
FIG. 3 depicts an example of an annotated slice of a 3D image data volume.

FIG. 3 depicts an example of a slice of an image volume of a knee including an annotated region 302 of a region of interest around the meniscus. The annotated ROI illustrates that a large part of the image data of the slice is not relevant for training the deep neural network. Hence, training the 3D deep neural network on the basis of 3D image data (voxels) contained in a VOI will significantly improve the performance of the system.

In an embodiment, the 3D localizer training module of FIG. 2 may comprise a processor 210 adapted to compute the centre location of a 3D bounding box on the basis of the sequence of images comprising the annotated 2D ROIs, wherein the 3D bounding box represents a VOI that encompasses 3D image data of the anatomical structure in a training data set. This process may be repeated for multiple sets of annotated images so that multiple bounding boxes for multiple sets of training data are generated.

An extractor module 211 may be configured to use the computed location of a 3D bounding box to extract 3D image data (voxels) of a VOI from a training data set of 3D image data 204 that was used to determine the 3D bounding box. Thereafter, a deep neural network 212 may be trained using the 3D image data contained in the determined 3D bounding boxes as input and the determined bounding box centres, their coordinates, as the target. The deep neural network may be trained using the distance between a predicted 3D bounding box centre (the output of the deep neural network) and the actual centre of a 3D bounding box as the loss function for a backpropagation until convergence process.

Hence, the training process executed by the localizer trainer module 115 in FIG. 1 may result in a 3D localizer 110 that pre-processes the training data before these are fed to the input of the 3D deep learning network. The 3D localizer includes a second trained deep neural network that generates coordinates of a centre of a VOI in the volume of a 3D image data training set (e.g. a sequence of medical images such as MRI images) that are provided to the input of the 3D localizer. On the basis of the centre of the VOI, the 3D localizer may determine the 3D image data 112 contained in the VOI and store the thus determined 3D image data in a memory of the system. In an embodiment, the dimensions of the VOI may be calculated as a percentile, e.g. a 95th percentile, of the dimensions of the 3D bounding boxes as determined for the training set as described with reference to FIG. 2.

As already described above, the training set includes 3D image data 112 as well as other data such as computer-readable text data of (relevant parts of) reports that include information on a pathology that is diagnosed by an expert, e.g. a doctor, on the basis of the 3D image training data. Hence, the 3D deep neural network may be trained using the 3D image training data contained in the VOI and target label values that may be indicative whether or not a certain pathology is present in the 3D image data.

In order to generate target label values for the training data, a label extractor module 126 may determine a target label value on the basis of the text of a report and store for each VOI a target label 128. Hence, in order to create a computer-readable target label value, the label extraction module 126 examines the content of the reports that are part of the training data converts the reports into a code (binary, or multivalued).

In an embodiment, the label extractor module may use a natural language processing method on phrases and/or words of a report such that presence or absence of such phrases and/or words may lead to a specific value or a specific value range for the target label. For example, the label extractor module may look for the presence or absence of specific words e.g. "large longitudinal meniscal tear", "small longitudinal meniscal tear", "no meniscal tear", etc., and determine a score on the basis of the presence or absence of such words.

In an embodiment, a decision tree may be created that describes how the presence or absence of one or more phrases and/or words determines the target label value and, optionally, under which conditions the target label cannot be determined. The decision tree may be programmed in a software application, which may be configured to process the full set of reports. A manual validation may be performed on a subset of the report set in order to determine accuracy of the labelling.

The 3D deep neural network for the pathology model may be trained on the basis of voxels of VOIs as provided by the 3D localizer and the associated target label values.

A common identifier may be used to link voxels of a VOI with a medical report and target label value. Depending on the specific anatomy and pathology, multiple series of one VOI, e.g. a primary and secondary series, may be used as input for the training and one target label value as output.

If the 3D image training data comprise multiple series, a position of a VOI may be determined on the basis of one of the multiple series of a VOI, e.g. a primary series. Therefore, the position of the VOI in the secondary series (i.e. the 3D image data not used by the 3D localizer) may be localized by mapping the coordinates of the VOI of the primary series onto the secondary series. The architecture of the 3D deep neural network may be a full 3D convolutional neural network (CNN) including a plurality of layers. The deep neural network may be implemented using a known deep learning framework.

The training of the deep neural network may include extraction of the VOI for each series of the training set and extraction of the target label for each study of the training set. Thereafter, the training set may be divided into a further training set and a validation set, wherein the further training set may be used to train the neural network by using an appropriate loss function for the target labels. The network is trained iteratively until the loss on the validation set converges.

After the training process, a trained 3D deep neural network representing a pathology model is obtained that is capable of: 1) receiving 3D image data of a VOI at its input, wherein the 3D image data include a predetermined anatomical structure for diagnosis; and, 2) generating a target label, i.e. a computer-generated sequence of words and/or phrases, e.g. in the form of a text string, indicating a determined pathology for at least part of the anatomical structure.

The computer-aided diagnostic system may be trained for different pathology models. For example, the 3D deep neural network may be trained for a pathology model that is adapted to detect meniscal tears in MRI images of knees, wherein target labels may include different values representing different target labels, e.g. two (binary) values for medial and lateral tears respectively.

The system described with reference to FIG. 1-3 was trained 22,000 medical images, i.e. sequences of MRI images. Based on the training the following performance is obtained on a test set of 5,500 images:

| Type | Sensitivity | Specificity | Accuracy | PPV | NPV |
|---|---|---|---|---|---|
| Medial meniscal tear | .83 | .95 | .91 | .91 | .91 |
| Lateral meniscal tear | .51 | .98 | .91 | .81 | .92 |

Figure 4:
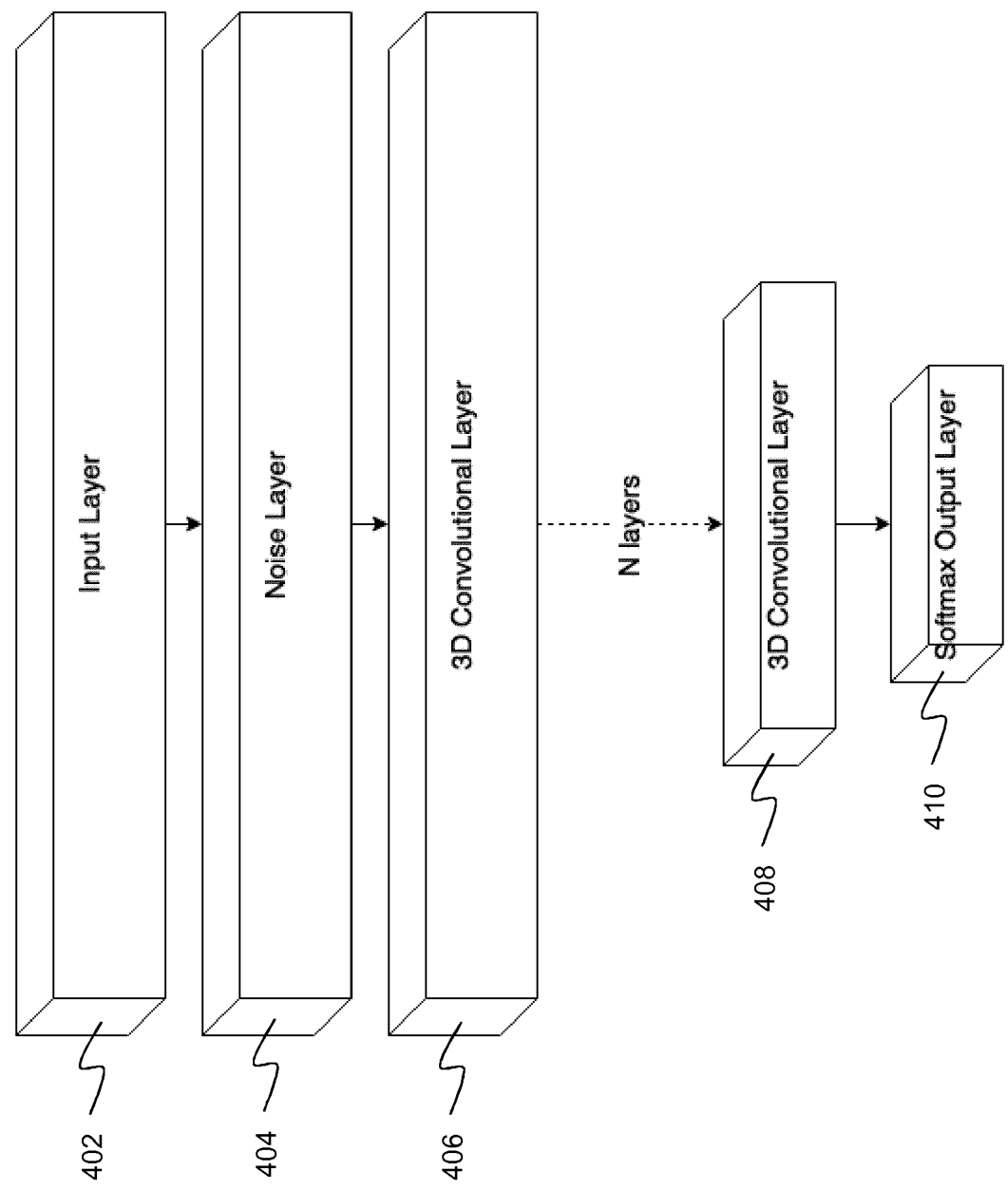
FIG. 4 schematically depicts a deep neural network architecture for modelling a localizer model according to an embodiment of the invention.

FIG. 4 schematically depicts a deep neural network architecture for use in the methods and systems described in this disclosure. In an embodiment, the deep neural network may be implemented using a 3D convolutional neural network (CNN) and trained as a 3D localizer as described with reference to FIG. 1-3 above. The network may comprise a noise layer 404 that adds distortion to the 3D input data that are provided to input layer 402. Additionally, no maxpooling layers are used. The noise layer may improve the generality of the model. The network may include a plurality of 3D convolutional layers 406,408 followed by a final Softmax layer 410.

The convolutional layers may use an Exponential Linear Unit (ELU) activation function. The target of the network is a tuple of (X,Y,Z) coordinates with a Mean Squared Error (MSE) loss. Minor variations in the number of layers and their definition, e.g. a different activation function like RELU and the use of additional regularization like dropout layers, may be used in the implementation of the convolutional neural network without losing the essential functioning of the deep neural network. Dropout layers may be used during training to reduce the problem of overfitting thereby increasing the generalization of the network for new data, i.e. data the network has not seen before.

Figure 5:
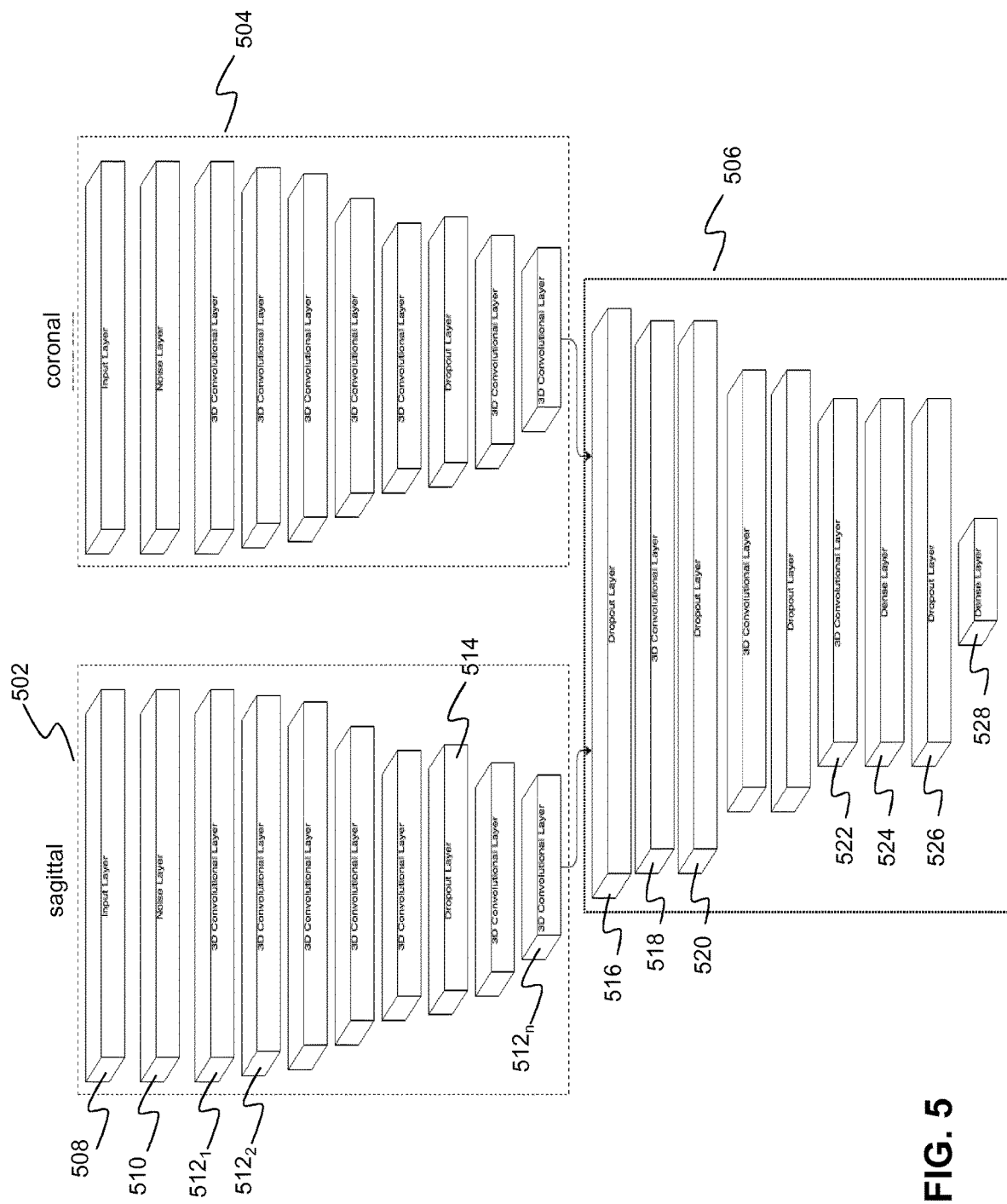
FIG. 5 schematically depicts a deep neural network architecture for modelling a pathology model according to an embodiment of the invention.

FIG. 5 schematically depicts another deep neural network architecture for use in the methods and systems described in this disclosure. In an embodiment, the deep neural network may be implemented using a 3D convolutional neural network (CNN) and trained as a 3D deep neural network that is adapted to generate a target label indicating a certain pathology when 3D image data of a VOI that image an anatomical structure are provided to the input of the network. As shown in FIG. 5, the neural network may include two pathways, a first pathway 502 defined by a first set of 3D convolutional layers designed to receive first voxels of the VOI derived from a first set of 3D image data (e.g. a primary sequence of images associated with a first image plane, e.g. a sagittal image plane) and a second pathway 504 defined by a second set of 3D convolutional layers designed to receive second voxels of the VOI derived from a second set of 3D image data (e.g. a secondary sequence of images associated with a second image plane, e.g. a coronal image plane).

The first and second deep neural network may have the similar architecture including a number of connected layers comprising an input layer 508, one or more noise layers 510 and a plurality of 3D convolutional layers $512_{1-n}$. Additionally, one or more dropout layers 514 may in inserted between the 3D convolutional layers. The output of the first and second deep neural network may be input to a third deep neural network 506 which receives the output of the first and second deep neural network at its input. The third deep neural network may include a plurality of 3D convolutional layers 518,522 separated by dropout layers 516,520,526. Additionally, the last layers of the third deep neural network may include one or more dense layers 524,528, i.e. fully connected layers for classifying a pathology.

Figure 6:
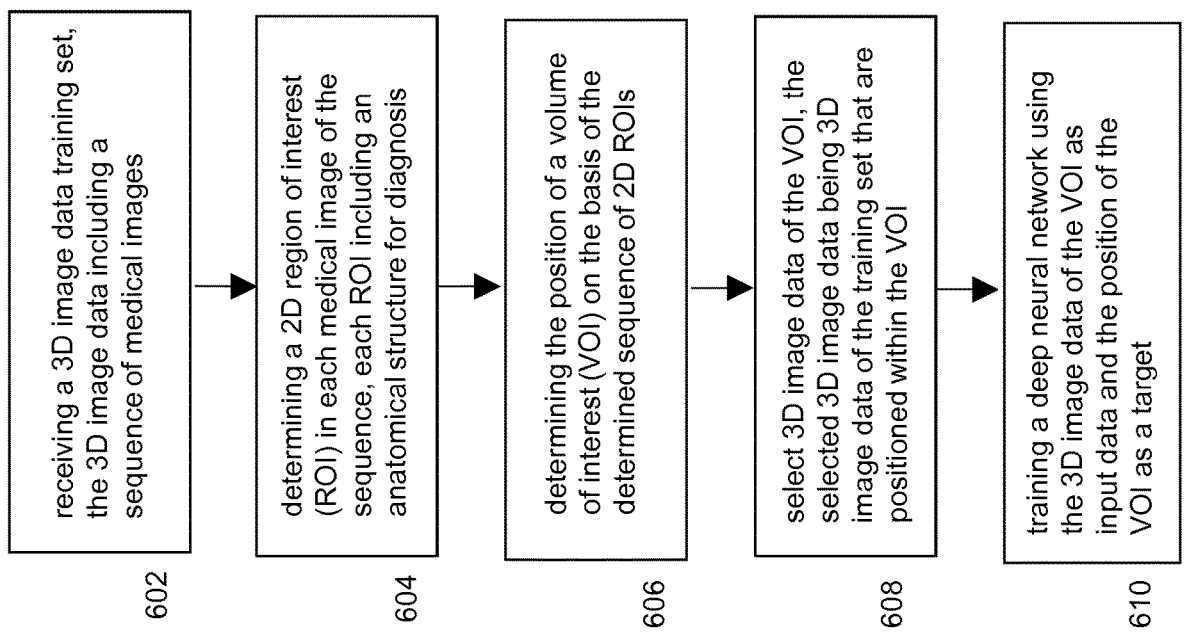
FIG. 6 schematically depicts a computer-implemented method of training a 3D deep neural network according to an embodiment of the invention.
Figure 7:
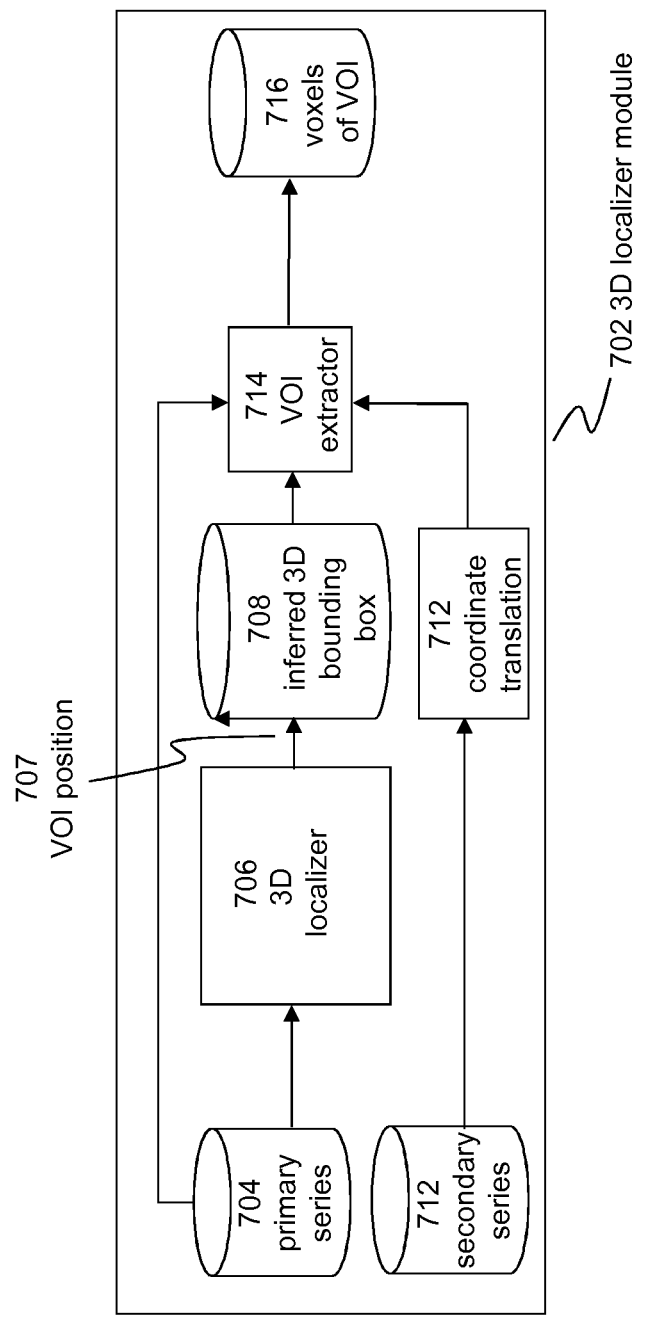
FIG. 7 depicts a 3D localizer module comprising a trained deep learning network according to an embodiment of the invention.

FIGS. 6 and 7 schematically depict a method for training a deep learning network system as a 3D localizer and a 3D localizer module including such trained deep learning network.

FIG. 6 schematically depicts a computer-implemented method of training a 3D deep neural network, preferably a first 3D convolutional neural network (CNN), for forming a 3D localizer model according to an embodiment of the invention. Such 3D localizer may comprise a trained 3D deep neural network that is adapted to receive 3D image data, e.g. voxels, of an anatomical structure as an input wherein the 3D image data are associated with a certain volume, which may be referred to as an image volume. The trained CNN may generate a target position of a VOI, i.e. a sub-volume of the image volume, containing 3D image data of a part of the anatomical structure that requires diagnosis.

The method may include the step of a computer receiving a 3D image data training set, wherein 3D image data may include a sequence of 2D medical images (step 602) and determining a 2D region of interest (ROI) in each of the images of the sequence of medical images (step 604). Here, a ROI may be a 2D closed contour of a particular shape, e.g. a rectangle, so that the ROI encloses a predetermined 2D area of pixels. Thereafter, a processor of the computer may construct a 3D bounding box on the basis of the ROIs, wherein the outer surfaces of the 3D bounding box defines a volume of interest (VOI) within the image volume of 3D image data of the training set (step 606). The position of the VOI within the image volume may be used to determine the 3D image data (voxels) that are contained in the VOI (step 608) and that are related to the anatomical structure that requires a diagnosis. The 3D image data of the VOI form a subset of 3D image data of the set of 3D image training data.

The 3D image data of the VOI are then used as input data for training a first deep neural network with the position of the VOI, e.g. a coordinate within the image volume, as target (step 610). This way, the trained first deep neural network may be adapted to receive 3D image data of an anatomical structure, e.g. a knee joint, and to generate a target position of a VOI that comprises part of the anatomic structure that requires diagnosis, e.g. a meniscus. The trained first deep neural network thus localizes a specific volume of voxels that can be used to efficiently train a further second deep neural network. The trained first deep neural network is capable of handling historical images and localizing a VOI therein.

FIG. 7 depicts a 3D localizer module comprising a trained deep learning network according to an embodiment of the invention. In particular, this figure illustrates a 3D localizer module 702, for localizing a volume of interest (VOI) in 3D image data according to a process as described with reference to FIG. 6. The module may be implemented as code on a computer and executed by a processor. The module may be arranged receive a first set of 3D image data, e.g. primary set of MRI images 704 associated with a first image plane (e.g. a sagittal image plane) and an associated second set of 3D image data, e.g. secondary set of MRI images 704 associated with a second image plane (e.g. a coronal image plane). The first set of 3D image data may be provided to the input of a deep neural network forming a 3D localizer 706, which is trained according to the process as described with reference to FIG. 6. The 3D localizer generates a position of VOI 707, that can be use by a processor in the computer to determine a 3D bounding box, a VOI. A VOI extractor may use 3D image data of the primary series and the 3D bounding box to extract voxels that are contained in the bounding box. Similarly, the module may map the coordinates of the 3D image data of the secondary series onto the coordinates of the first series. Thereafter, it may use the calculated 3D bounding box to extract voxels contained in the box. This way, sets of voxels are determined that represent the VOI 716.

Figure 8:
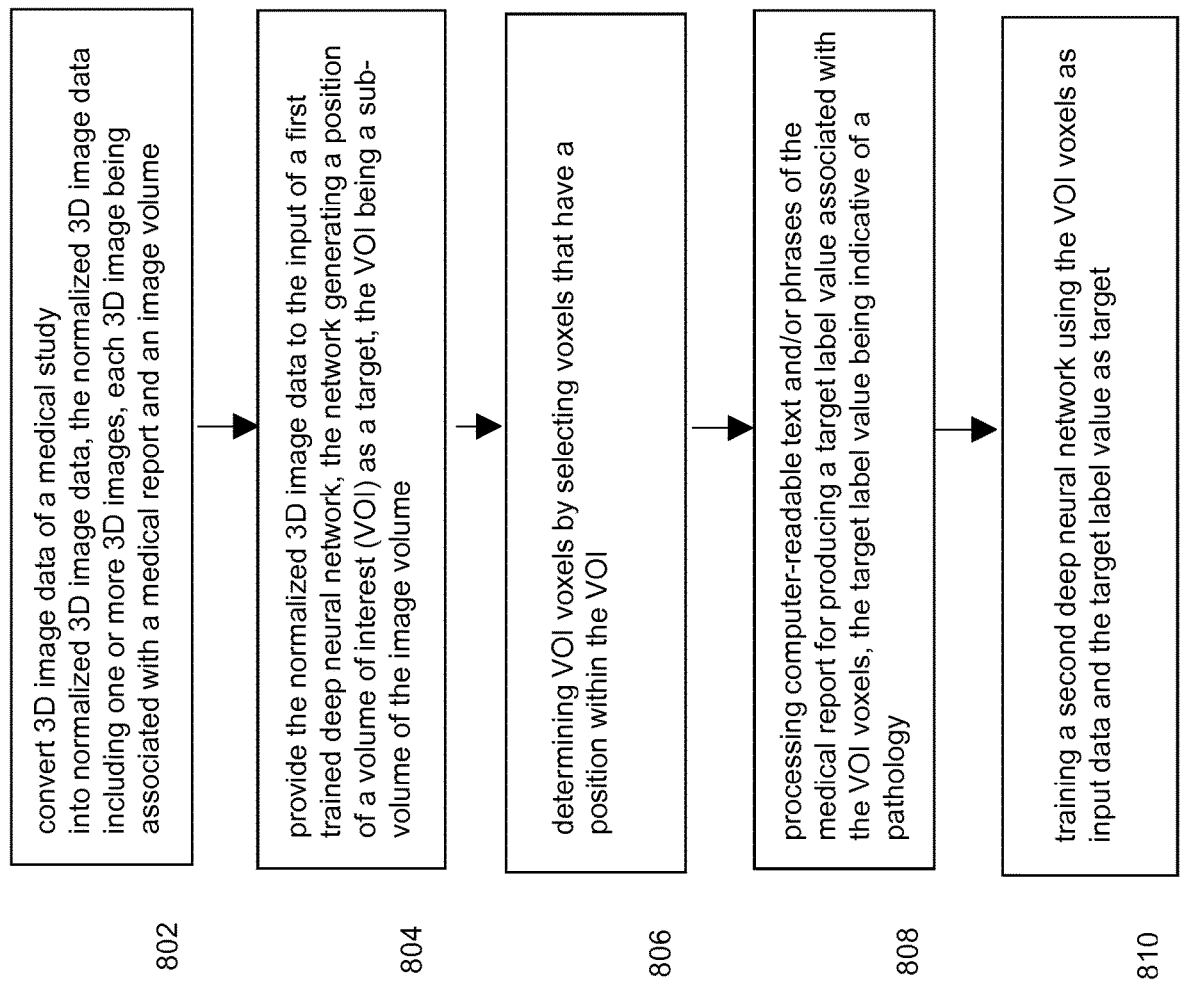
FIG. 8 schematically depicts a computer-implemented method of training a 3D deep neural network according to another embodiment of the invention.

FIG. 8 schematically depicts a computer-implemented method of training a 3D deep neural network, preferably a 3D convolutional neural network (CNN), for forming a pathology model on the basis of a training set. The training set may include training data of multiple medical studies, wherein each medical study includes 3D image data (voxels) in the form of one or more sequences of medical images and computer-readable text and/or phrases of at least one medical report associated with the 3D image data. Here, the 3D image data of one medical study may include primary 3D image data including a sequence of primary medical images and associated secondary 3D image data including a sequence of secondary medical images. The training data of one medical study, e.g. the 3D image data and the associated computer-readable text and/or phrases may be stored in a database. A common identifier may be used to link 3D image data to data associated with a medical report.

In a first step, 3D image data of a training set may be normalized into normalized 3D image data (step 802). The normalized 3D image data of each medical study may be provided to an input of a first trained neural network, that is adapted to generate for each medical study a target position of a VOI within the volume of normalized 3D image data (step 804). In an embodiment, only the normalized primary 3D image data may be used for generating a target position of the VOI. In that case, a known coordinate mapping between the primary and secondary 3D image data may be used to determine the target position of the VOI in the secondary 3D image data.

The target position of a VOI may then be used to select voxels in the image volume of the 3D image data that are positioned within the VOI (step 806). Further, a natural language processing method may be used to process computer-readable text and/or phrases of each medical report in order to produce a target label value for the voxels of a VOI (step 808). Thereafter, sets of VOI voxels and associated target label values, are then used as input data for training a second neural network with the target label values as a target (step 810).

Figure 9:
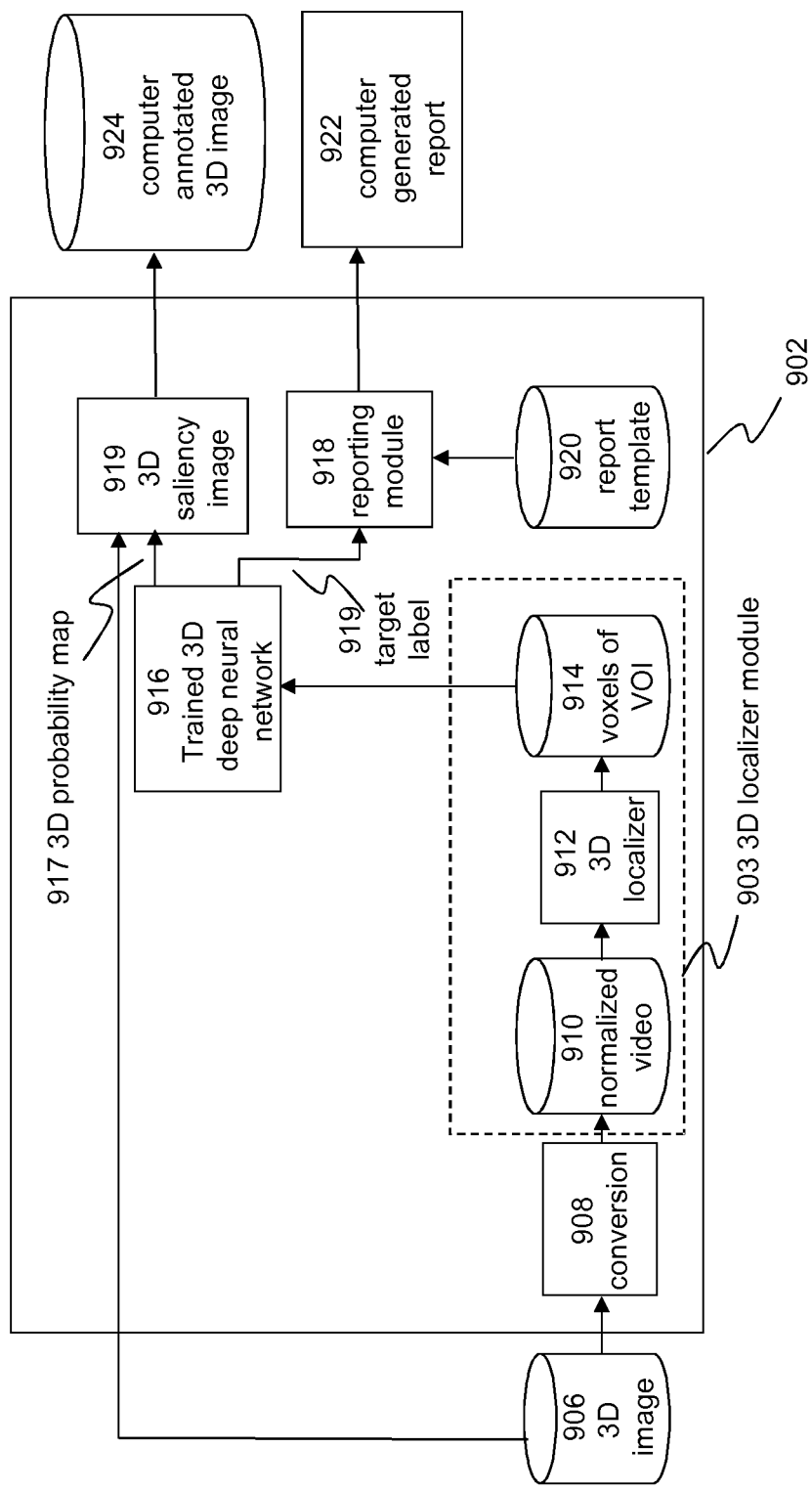
FIG. 9 schematically depicts a computer system for computer-aided diagnostics using 3D deep neural networks according to an embodiment of the invention.

FIG. 9 schematically depicts a computer system for computer-aided diagnostics using 3D deep neural networks according to an embodiment of the invention. This figure represents a computer system 902 that comprises deep neural networks that are trained in accordance with the processes described with reference to FIG. 1-8.

The computer system may be executed in an inference mode, wherein the computer system comprises a 3D localizer module 903 including a 3D localizer 912 comprising a 3D deep neural network for determining the position of a VOI in 3D image 906 (e.g. a sequence of medical images such as MRI or CT images) that is provided to the input of the computer system. This 3D deep neural network may be trained according to a process as described with reference to FIG. 6.

The 3D image may be converted and normalized using a conversion module 908, stored in a database 912. The normalized 3D image data (voxels) may be provided to the 3D localizer in order to determine voxels that are contained within a volume of interest (VOI) in the image volume of the 3D image. The voxels that are contained within a VOI may be stored in a database 914 and provided to the input of a 3D deep neural network 916, which may be trained according to a process as described with reference to FIG. 8.

The output of the trained 3D deep neural network 916 may be one or more target labels, each being associated with a target label value. The target labels may be used by a reporting module 918 to generate a computer-generated report 922. The target label value may report if a certain pathology has been determined or not. For example, if a target label value is within a predetermined first range, the computer may determine that the pathology is detected. In that case, the computer may generate a first text string describing that a certain pathology, e.g. a meniscus tear, has been determined. Alternatively, if a target label value is within a predetermined second range, the computer may determine that no pathology has been determined. In that case, the computer may generate a second text string describing that a certain pathology, e.g. a meniscus tear, has not been determined. The reporting module may use a report template and the text strings to generate a computer-generated report. The reporting module may be configured to insert the computer-generated text in a report template which may also include other data, e.g. patient data and data associated with the physician. The report may include text associated with a diagnosis.

Additionally, the report may include one or more images, preferably annotated images, e.g. a slice of a computer generated annotated 3D image. The visualisation may be used to explain why the model decided that the target label has its predicted value. Such 3D visualisation of the pathology is very valuable as feedback to the physician who interprets the model result. The visual feedback may be determined on the basis of a 3D saliency map that may be used to provide a colour/intensity indication to voxels in the VOI, wherein the colour/intensity indication provides information to the physician how relevant each voxel in the VOI contributed to the target label.

The 3D saliency map may be generated by a processor that adapted using a modified guided backpropagation process that is suitable for 3D datasets. A conventional process of guided backpropagation for a 2D dataset is described in the article by Springenberg et al., *"Striving for simplicity: the all convolutional net"*, 3rd International Conference on Learning Representations, ICLR 2015. The guided backpropagation process described in the article was used for visualizing representations learned by higher layers of a 2D convolutional network. The method uses the output of the penultimate network layer (before the softmax classifier) as the input for the backpropagation step in order to determine which pixels are most salient for classification.

The processor of the computer system in FIG. 9 uses a guided backpropagation process for generating a 3D saliency image. In the guided backpropagation process, the gradient of the network's prediction (at the output) with respect to the input is calculated holding the weight parameters fixed. Hence, a 3D probability map 917 may be used as input to the backpropagation process. The 3D probability map is formed when the 3D image data, i.e. the voxels, associated with the VOI as determined by the first neural network propagate through the trained 3D deep neural network 916 in the forward direction.

The 3D probability map associated with the 3D image data set may be extracted from a 3D convolutional layer that is positioned before the fully connected classification layer (one of the 'dense' layers). This 3D probability map may be used as input for the backpropagation process. Hence, in the system as depicted in FIG. 9, the processor does not use the target label for the input of the backpropagation process. Instead, it uses the predicted probability of a positive result, e.g. the 3D probability map of an 3D image that is present in the last 3D convolutional layer (or one of the last 3D convolutional layers) of a deep neural network system as depicted in FIG. 5, e.g. 3D convolutional layer $522_1$ or $522_2$ before the (dense) fully connected layers 524,528.

Only the positive part of the output of the guided backpropagation process, i.e. max(output,0), is used in determining the amount that each voxel contributes to the positive result. The output of the guided backpropagation process includes a 3D saliency image which may be used identify voxels in the VOI e.g. by applying a certain intensity to voxels. The intensity may scale with the saliency values as determined during the backpropagation process, wherein it is assumed that saliency values are the highest for voxels that represent the pathology. This way, the saliency map may be combined with the 3D image data in order to visualize voxels in the 3D image data that provide a substantial contribution in the outcome of the target label. The thus computer-annotated 3D image may be stored on a storage medium 924.

FIG. 10 depicts an example of a report that is generated using a system for computer-aided diagnostics according to an embodiment of the invention. As shown in this figure, the report 1002 comprise computer-generated text strings that explains the findings of the neural network, e.g. a longitudinal meniscal tear 1004 and other information 1006 regarding ligaments or the like. Additionally, the report may include one or more images, e.g. a slice of annotated 3D image data which indicate the voxels in a VOI 1008 that contributed for a substantial part to the target label, in particular a target label associated with a positive result.

Figure 11:
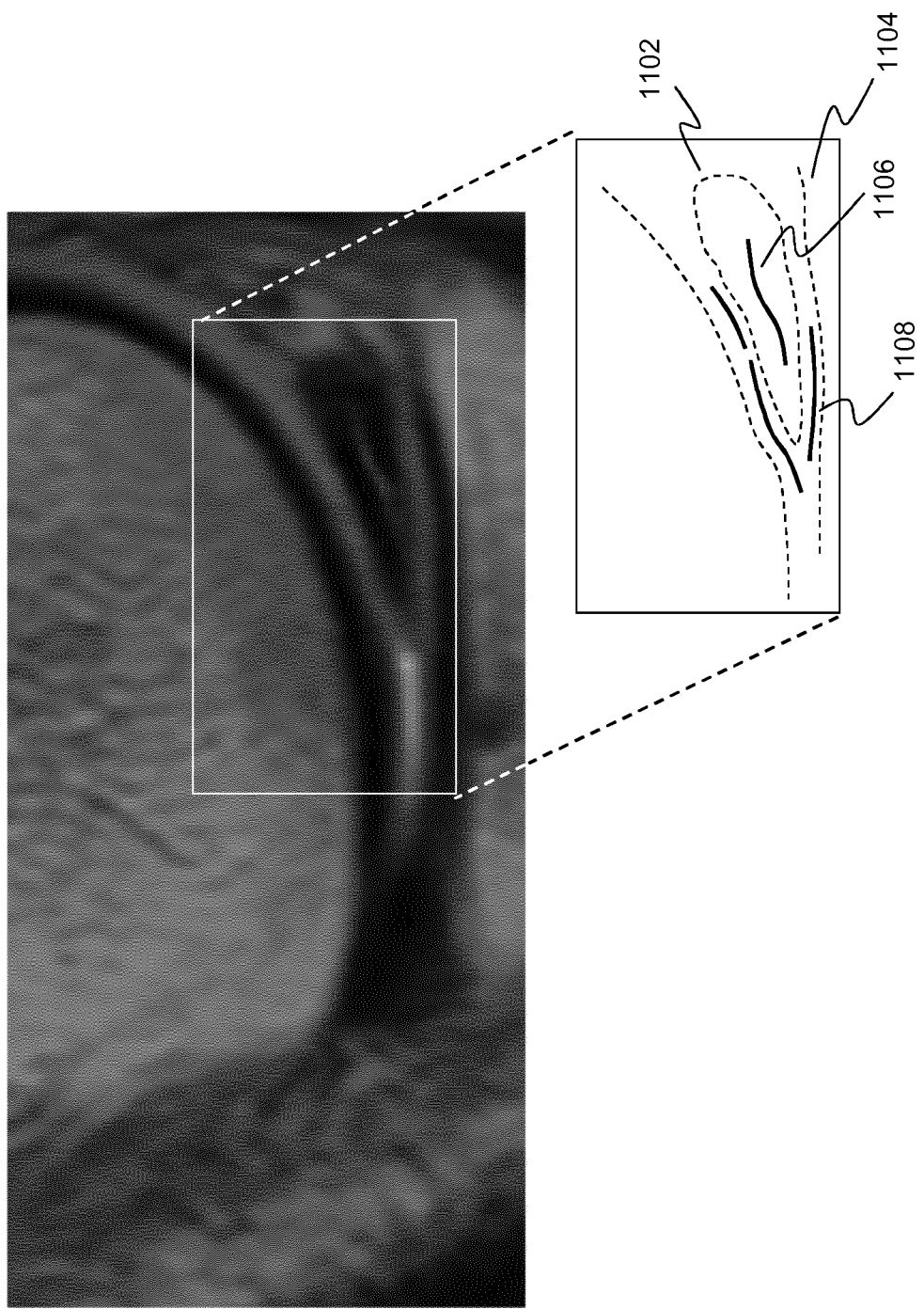
FIG. 11 depicts an example of an annotated image of a slice of a VOI that is generated by a system for computer-aided diagnostics according to an embodiment of the invention.

FIG. 11 depicts an example of an annotated image of a slice of a VOI that is generated by a system for computer-aided diagnostics according to an embodiment of the invention. The saliency is shown as shades of colors where the highest saliency has the brightest value. In this example a 2D slice of a full 3D saliency map is shown. As schematically shown in the inset, the dotted line indicates the contours of bone structures and the solid lines indicates groups of voxels that were identified by the guided backpropagation process to provide a high or at least a substantial contribution to the target label, in this case a positive finding of a longitudinal meniscal tear as reported in the report of FIG. 10.

Figure 12:
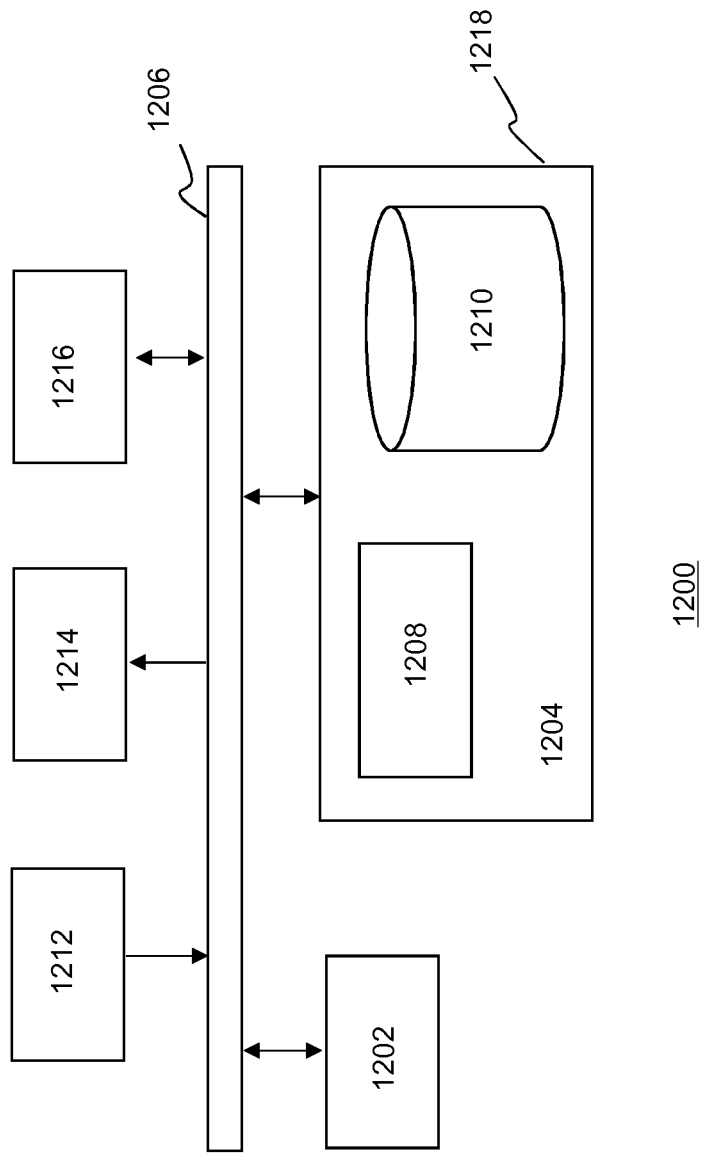
FIG. 12 is a block diagram illustrating an exemplary data processing system that may be used in diagnostic system as described in this disclosure.

FIG. 12 is a block diagram illustrating exemplary data processing systems described in this disclosure. Data processing system 1200 may include at least one processor 1202 coupled to memory elements 1204 through a system bus 1206. As such, the data processing system may store program code within memory elements 1204. Further, processor 1202 may execute the program code accessed from memory elements 1204 via system bus 1206. In one aspect, data processing system may be implemented as a computer that is suitable for storing and/or executing program code. It should be appreciated, however, that data processing system 1200 may be implemented in the form of any system including a processor and memory that is capable of performing the functions described within this specification.

Memory elements 1204 may include one or more physical memory devices such as, for example, local memory 1208 and one or more bulk storage devices 1210. Local memory may refer to random access memory or other non-persistent memory device(s) generally used during actual execution of the program code. A bulk storage device may be implemented as a hard drive or other persistent data storage device. The processing system 1200 may also include one or more cache memories (not shown) that provide temporary storage of at least some program code in order to reduce the number of times program code must be retrieved from bulk storage device 1210 during execution.

Input/output (I/O) devices depicted as input device 1212 and output device 1214 optionally can be coupled to the data processing system. Examples of input device may include, but are not limited to, for example, a keyboard, a pointing device such as a mouse, or the like. Examples of output device may include, but are not limited to, for example, a monitor or display, speakers, or the like. Input device and/or output device may be coupled to data processing system either directly or through intervening I/O controllers. A network adapter 1216 may also be coupled to data processing system to enable it to become coupled to other systems, computer systems, remote network devices, and/or remote storage devices through intervening private or public networks. The network adapter may comprise a data receiver for receiving data that is transmitted by said systems, devices and/or networks to said data and a data transmitter for transmitting data to said systems, devices and/or networks. Modems, cable modems, and Ethernet cards are examples of different types of network adapter that may be used with data processing system 1250.

As pictured in FIG. 12, memory elements 1204 may store an application 1218. It should be appreciated that data processing system 1200 may further execute an operating system (not shown) that can facilitate execution of the application. Application, being implemented in the form of executable program code, can be executed by data processing system 1200, e.g., by processor 1202. Responsive to executing application, data processing system may be configured to perform one or more operations to be described herein in further detail.

In one aspect, for example, data processing system 1200 may represent a client data processing system. In that case, application 1218 may represent a client application that, when executed, configures data processing system 1200 to perform the various functions described herein with reference to a "client". Examples of a client can include, but are not limited to, a personal computer, a portable computer, a mobile phone, or the like.

In another aspect, data processing system may represent a server. For example, data processing system may represent an (HTTP) server in which case application 1218, when executed, may configure data processing system to perform (HTTP) server operations. In another aspect, data processing system may represent a module, unit or function as referred to in this specification.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A computer-implemented method for determining a pathology in three-dimensional (3D) image data, the method comprising steps of:
   receiving at least a first 3D image of a body part, the first 3D image comprising voxels associated with a predetermined image volume;
   providing the first 3D image to an input of a trained first 3D convolutional neural network, the trained first 3D convolutional network being trained to determine a position of a volume of interest (VOI) in the image volume of the first 3D image, the VOI being associated with a part of the body part, the VOI defining a sub-volume of the image volume;
   receiving a position of the VOI from an output of the trained first 3D convolutional neural network and determining first VOI voxels by selecting voxels of the first 3D image that have a position within the VOI;
   providing the first VOI voxels to an input of a trained second 3D convolutional neural network, the trained second 3D convolutional neural network being trained to determine a label value based on voxel values of at least the first VOI voxels, the label value being indicative of a presence or absence of the pathology in the VOI; and,
   receiving the label value associated with the first VOI from an output of the trained second 3D convolutional neural network and generating a medical report by associating the label value with text and/or sentences representing a description of the pathology.

2. The method according to claim 1 further comprising steps of:
   retrieving a 3D probability map associated with the VOI voxels from a convolutional layer of the trained second 3D convolutional neural network and using the 3D probability map as input to a backpropagation process for generating a 3D saliency map associated with the VOI voxels; and
   generating an annotated 3D image of the pathology in the VOI by using the 3D saliency map to identify voxels in the VOI that made a substantial contribution to the determination of the label value by the trained second 3D convolutional neural network.

3. The method according to claim 2 further comprising a step of:
   inserting the annotated 3D image or one or more two-dimensional (2D) slices of the annotated 3D image in the report.

4. The method according to claim 1, wherein the first 3D image includes a sequence of images of a first image plane, the method further comprising steps of:
   receiving a second 3D image of the body part, the second 3D image including a sequence of images of a second image plane;
   determining second VOI voxels by selecting voxels of the second 3D image that have a position within the VOI; and
   the trained second 3D convolutional neural network determining a label value on the basis of the first and second VOI voxels.

5. The method according to claim 4 wherein the trained second 3D convolutional neural network includes at least a first plurality of 3D convolutional neural network layers forming a first pathway through the trained second 3D convolutional neural network and a second plurality of 3D convolutional neural network layers forming a second pathway through the trained second 3D convolutional neural network, the first plurality of 3D convolutional neural network layers being configured to process the first VOI voxels and the second plurality of 3D convolutional neural network layers being configured to process the second VOI voxels.

6. The method according to claim 1, wherein one or both of the trained first and second 3D convolutional neural network includes one or more noise layers.

7. A computer-implemented method for training one or more 3D convolutional neural networks in a system that is configured to determine a pathology of a body part in 3D image data, the method comprising steps of:
   a computer receiving a 3D image data training set of a medical study, the 3D image data training set comprising 3D images of the body part, a 3D image comprising voxels associated with a predetermined image volume and being associated with a medical report comprising computer-readable text parts and/or sentences indicative of an absence or presence of the pathology in the 3D image;
   for each said 3D image of the 3D image training data, the computer forming a 3D bounding box, the 3D bounding box forming a sub-volume in the predetermined image volume of the 3D image, the sub-volume defining a volume of interest (VOI), the VOI including a part of the body part that may comprise the pathology;
   for each said 3D image of the 3D image training data, the computer determining a position of the VOI in the predetermined image volume and determining voxels that are positioned in the VOI; and,
   the computer training a first 3D convolutional neural network using the voxels of each said VOI as input and the position of each said VOI as targets, the first 3D convolutional neural network being trained to determine a position of a volume of interest (VOI) in the image volume of the first 3D image;

for each said 3D image of the 3D image training data, the computer processing computer-readable text and/or phrases of the medical report associated with the VOI for the 3D image using natural-language processing for producing a target label value, the target label value being indicative of an absence or presence of the pathology of the body part in the VOI for the 3D image; and, the computer training a second 3D convolutional neural network using the voxels of each said VOI as input and the target label values associated with each said VOI as targets, the second 3D convolutional neural network being trained to determine a label value based on voxel values of the voxels, the label value being indicative of a presence or absence of the pathology in the VOI.

8. The method according to claim 7 wherein said processing computer-readable text and/or phrases includes:

the computer using a decision tree for describing how an absence or presence of one or more phrases and/or words in the computer-readable text parts and/or sentences of the medical report determines the target label value.

9. A neural network system implemented on a computer, the system comprising one or more trained 3D convolutional neural networks, wherein the one or more trained 3D convolutional neural networks are trained in by performing the method steps of:

a computer receiving a 3D image data training set of a medical study, the 3D image data training set comprising 3D images of the body part, a 3D image comprising voxels associated with a predetermined image volume and being associated with a medical report comprising computer-readable text parts and/or sentences indicative of an absence or presence of the pathology in the 3D image;

for each said 3D image of the 3D image training data, the computer forming a 3D bounding box, the 3D bounding box forming a sub-volume in the predetermined image volume of the 3D image, the sub-volume defining a volume of interest (VOI), the VOI including a part of the body part that may comprise the pathology;

for each said 3D image of the 3D image training data, the computer determining a position of the VOI in the predetermined image volume and determining voxels that are positioned in the VOI; and the computer training a first 3D convolutional neural network using the voxels of each said VOI as input and the position of each said VOI as targets, the first 3D convolutional neural network being trained to determine a position of a VOI in the image volume of the first 3D image;

for each said 3D image of the 3D image training data, the computer processing computer-readable text and/or phrases of the medical report associated with the VOI for the 3D image using natural-language processing for producing a target label value, the target label value being indicative of an absence or presence of the pathology of the body part in the VOI for the 3D image; and the computer training a second 3D convolutional neural network using the voxels of each said VOI as input and the target label values associated with each said VOI as targets, the second 3D convolutional neural network being trained to determine a label value based on voxel values of the voxels, the label value being indicative of a presence or absence of the pathology in the VOI.

10. A computer system adapted to determine a pathology in three-dimensional (3D) image data, the computer system comprising:

a storage medium having computer readable program code stored therein, the code including trained first and second 3D convolutional neural networks, and one or more processors, coupled to the computer readable storage medium, wherein upon executing the computer readable program code, the system carrying out operations comprising:

receiving at least a first 3D image of a body part, the first 3D image comprising voxels associated with a predetermined image volume;

providing the first 3D image to an input of the trained first 3D convolutional neural network, the trained first 3D convolutional network being trained to determine a position of a volume of interest (VOI) in the image volume of the first 3D image, the VOI being associated with a part of the body part, the VOI defining a sub-volume of the image volume;

receiving a position of the VOI from an output of the trained first 3D convolutional neural network and determining first VOI voxels by selecting voxels of the first 3D image that have a position within the VOI;

providing the first VOI voxels to an input of the trained second 3D convolutional neural network, the trained second 3D convolutional neural network being trained to determine a label value based on voxel values of at least the first VOI voxels, the label value being indicative of a presence or absence of the pathology in the VOI; and, receiving the label value associated with the first VOI from an output of the trained second 3D convolutional neural network and generating a medical report by associating the label value with text and/or sentences representing a description of the pathology.

11. The computer system according to claim 10 wherein the operations further comprise:

retrieving a 3D probability map associated with the VOI voxels from a convolutional layer of the second convolutional neural network and using the 3D probability map as input to a backpropagation process for generating a 3D saliency map associated with the VOI voxels; and generating an annotated 3D image of the pathology in the VOI by using the 3D saliency map to identify voxels in the VOI that made a substantial contribution to the determination of the label value by the trained second 3D convolutional neural network.

12. The computer system according to claim 11 wherein the operations further comprise:

inserting the annotated 3D image or one or more two-dimensional (2D) slices of the annotated 3D image in the report.

13. The computer system according to claim 10, wherein the first 3D image includes a sequence of images of a first image plane, and wherein the operations further comprise:

receiving a second 3D image of the body part, the second 3D image including a sequence of images of a second image plane;

determining second VOI voxels by selecting voxels of the second 3D image that have a position within the VOI; and the trained second 3D convolutional neural network, determining a label value on the basis of the first and second VOI voxels.

14. The computer system according to claim 13 wherein the trained second 3D convolutional neural network includes at least a first plurality of 3D convolutional neural network layers forming a first pathway through the trained second 3D convolutional neural network and a second plurality of 3D convolutional neural network layers forming a second pathway through the trained second 3D convolutional neural network, the first plurality of 3D convolutional neural network layers being configured to process the first VOI voxels and the second plurality of 3D convolutional neural network layers being configured to process the second VOI voxels.

15. A non-transitory computer program product comprising software code portions configured for, when run in the memory of a computer, executing the method steps of:
  receiving at least a first 3D image of a body part, the first 3D image comprising voxels associated with a predetermined image volume;
  providing the first 3D image to an input of a trained first 3D convolutional neural network, the trained first 3D convolutional network being trained to determine a position of a volume of interest (VOI) in the image volume of the first 3D image, the VOI being associated with a part of the body part, the VOI defining a sub-volume of the image volume;
  receiving a position of the VOI from an output of the trained first 3D convolutional neural network and determining first VOI voxels by selecting voxels of the first 3D image that have a position within the VOI;
  providing the first VOI voxels to an input of a trained second 3D convolutional neural network, the trained second 3D convolutional neural network being trained to determine a label value based on voxel values of at least the first VOI voxels, the label value being indicative of a presence or absence of the pathology in the VOI; and
  receiving the label value associated with the first VOI from an output of the trained second 3D convolutional neural network and generating a medical report by associating the label value with text and/or sentences representing a description of the pathology.

16. The method as claimed in claim 1, wherein the generating of the medical report including if the label value is within a predetermined first range, comprises steps of
  determining a first text string describing that the pathology has been detected and if a label value is within a predetermined second range,
  determining a second text string describing that the pathology has not been detected; and,
  optionally, inserting the first text string or second text string into a text string representing a report template.

17. The method of claim 7, wherein the formation of the 3D bounding box is based on 2D regions of interest (ROIs) in slices of the 3D image.

18. The method of claim 4, wherein the first image plane is a sagittal plane and the second image plane is a coronal plane.

19. The computer system of claim 13, wherein the first image plane is a sagittal plane and the second image plane is a coronal plane.

* * * * *